United States Patent
Maas et al.

(10) Patent No.: US 11,812,937 B2
(45) Date of Patent: Nov. 14, 2023

(54) APPARATUS, METHOD AND MEDIUM FOR PREDICTING AND DISPLAYING A FERTILITY WINDOW OF A WOMAN

(71) Applicant: KONINKLIJKE PHILIPS N.V., Eindhoven (NL)

(72) Inventors: Joost Hubert Maas, Helmond (NL); Emiel Peeters, Eindhoven (NL); Sima Asvadi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 440 days.

(21) Appl. No.: 16/309,948

(22) PCT Filed: Jun. 1, 2017

(86) PCT No.: PCT/EP2017/063241
§ 371 (c)(1),
(2) Date: Dec. 14, 2018

(87) PCT Pub. No.: WO2017/215920
PCT Pub. Date: Dec. 21, 2017

(65) Prior Publication Data
US 2019/0167236 A1    Jun. 6, 2019

Related U.S. Application Data

(60) Provisional application No. 62/349,349, filed on Jun. 13, 2016.

(51) Int. Cl.
*A61B 10/00* (2006.01)
*A61B 5/00* (2006.01)
(Continued)

(52) U.S. Cl.
CPC ........ *A61B 10/0012* (2013.01); *A61B 5/0013* (2013.01); *A61B 5/01* (2013.01);
(Continued)

(58) Field of Classification Search
CPC ... A61B 10/0012; A61B 5/103; A61B 5/1032; A61B 5/0013; A61B 2010/0016–0032;
(Continued)

(56) References Cited

U.S. PATENT DOCUMENTS

| 5,512,841 A | * | 4/1996 | Gibson | G01R 31/2839 324/121 R |
| 7,099,880 B2 | * | 8/2006 | Arning | G06F 16/2465 |

(Continued)

FOREIGN PATENT DOCUMENTS

| WO | WO2011070577 A2 | 6/2011 |
| WO | WO2014159846 A1 | 10/2014 |

(Continued)

OTHER PUBLICATIONS

Manning, J. T., et al. "Asymmetry and the menstrual cycle in women." Ethology and Sociobiology 17.2 (1996): 129-143. (Year: 1996).*

(Continued)

*Primary Examiner* — David J. McCrosky (57) ABSTRACT

An apparatus and method for predicting a fertility window include an image capture device and a processor. The fertility window includes a period of increased fecundability for a woman based on optical monitoring of facial features. The image capture device is configured to record images including facial features of a subject. The processor is configured to receive data corresponding to the recorded plural images; determine from the data changes in the facial features; and predict a fertility window based on the determination.

18 Claims, 6 Drawing Sheets

(51) Int. Cl.
  *G06T 7/00*    (2017.01)
  *A61B 5/103*   (2006.01)
  *G06V 40/16*   (2022.01)
  *G06V 40/10*   (2022.01)
  *A61B 5/01*    (2006.01)

(52) U.S. Cl.
  CPC ............ *A61B 5/103* (2013.01); *G06T 7/0014* (2013.01); *G06V 40/15* (2022.01); *G06V 40/172* (2022.01); *A61B 2010/0019* (2013.01); *G06V 40/165* (2022.01)

(58) Field of Classification Search
  CPC ........ A61B 5/742–745; G06K 9/00288; G06T 7/0014; G16H 10/00–80/00
  See application file for complete search history.

(56) References Cited

U.S. PATENT DOCUMENTS

| | | | | |
|---|---|---|---|---|
| 8,374,989 | B2* | 2/2013 | Lee ................... | A61B 10/0012 706/52 |
| 8,764,656 | B2* | 7/2014 | Shin .................. | A61B 5/1123 600/301 |
| 10,614,288 | B2* | 4/2020 | Kusens ............... | G06T 7/0016 |
| 10,765,408 | B2* | 9/2020 | Qi ..................... | A61B 10/0012 |
| 2002/0135462 | A1* | 9/2002 | Nels .................. | H04L 51/212 340/7.3 |
| 2013/0131973 | A1* | 5/2013 | Friedler ............. | G01S 5/0252 701/408 |
| 2015/0118663 | A1 | 4/2015 | Levy | |

FOREIGN PATENT DOCUMENTS

| WO | WO2015105217 A1 | 7/2015 |
|---|---|---|
| WO | WO2015150434 A1 | 10/2015 |

OTHER PUBLICATIONS

Krol, J. CNET.com "Philips developing camera that can monitor your vital signs just by watching you" Jun. 9, 2016. <https://www.cnet.com/science/philips-developing-camera-that-can-monitor-your-vital-signs-just-by-watching-you/> (Year: 2016).*

Scutt, et al.: "Symmerty and ovulation in wormen", Human Reproduction, vol. 11 No. 11, pp. 2477-2480, 1996.

Roberts, S.C. et al., "Female Facial Attractiveness Increases During the Fertile Phase of the Menstrual Cycle", Proceedings of the Royal Society B: Biological Sciences, 2004 the Royal Society, pp. S270-S272, Aug. 2004.

PCT International Search Report, International application No. PCT/EP2017/063241, dated Aug. 30, 2017.

Observations on the PCT International Search Report and the Written Opinion of International Application No. PCT/EP2017/063241, dated Nov. 21, 2017.

Cetinkaya, et al: "Testing the Concealed Ovulation Hypothesis in the Framework of Facial Symmetry Fluctuations Moderated by Menstrual Cycle in Women", Turkish Journal of Psychology, vol. 25, No. 55, Abstract in English.

Burriss, et al: "Changes in Women's Facial Skin Color over the Ovulatory Cycle are Not Detectable by the Human Visual System", PloS one, pp. 1-16.

* cited by examiner

APPARATUS, METHOD AND MEDIUM FOR PREDICTING AND DISPLAYING A FERTILITY WINDOW OF A WOMAN

CROSS-REFERENCE TO RELATED APPLICATIONS

This patent application claims the priority benefit under 35 U.S.C. § 371 of international patent application no. PCT/EP2017/063241, filed Jun. 1, 2017, which claims the priority benefit under 35 U.S.C. § 119(e) of U.S. Provisional Application No. 62/349,349 filed on Jun. 13, 2016, the contents of which are hereby incorporated by reference herein.

FIELD OF THE INVENTION

The present invention is generally related to image analysis, and more specifically, to image analysis for use in fertility monitoring.

BACKGROUND OF THE INVENTION

In most developed countries, about fifteen percent (15%) of couples are unable to get pregnant after one year of unprotected sex. Infertility can be traced to the woman in one third of the cases and in another third of the cases, the cause lies with the man. In all other instances, there are multiple factors or no cause can be found. Globally, the number of couples with infertility issues was found to be 48.5 million in 2010, and the couples dealing with fertility problems have to cope with a lot of frustration and disappointment that can have a significant impact on their lives. There can be many causes underlying the fertility problems, but in most cases, a first step towards treatment of infertility is to increase fertility awareness and to predict a fertility window. The fertility window is defined as the six (6) days before the day of ovulation plus the period (e.g., days) of ovulation. Sexual intercourse within the fertility window is essential for successful conception. There exists a few common methods for the prediction of the fertility window, including Basal Body temperature (BBT) charting, Cervical Mucous Monitoring (CCM), electrolyte levels in saliva, and monitoring of the Luteinizing Hormone (LH) level in urine.

From a different family planning perspective, although use of modern contraceptives is still rising from 54% in 1990 to 57.4% in 2014, there are still millions of women, especially in developing countries, who depend and/or rely on Natural Family Planning (NFP) to prevent unintended pregnancies. There are several different methods for NFP including Standard Day Method, Basal Body Temperature method, Two Day Method, and Sympto-thermal method with effectiveness to prevent pregnancies in the range from 75%-99%. All these methods have in common that they are predictors for the fertility window of the woman.

The above description shows that an accurate prediction of the fertility window is important both in increasing the chance of a successful conception for couples with infertility issues as well as for reducing the risk of unintended pregnancies for women who depend/rely on NFP. However, current offerings of female fertility tests and methods to predict the fertility window require disciplined, repetitive action of the woman and, in this way, pose additional stress on women who already have to deal with the frustration and disappointment of not getting pregnant while they are actively trying over a longer period of time. Another technique is suggested in the 2004 on-line publication of the Royal Society of Biology Letters article, entitled, "Female Facial Attractiveness Increases during the Fertile Phase of the Menstrual Cycle," by S. Craig Roberts et al. In that article, the authors recognize that facial appearance might also be subject to cyclical variation and be perceived by potential mates, particularly in view of the key role that facial attractiveness plays in human mate choice. The authors surveyed men and women based on photographs of various women and found that women's faces were judged to be more attractive during the fertile window of the menstrual than during the luteal phase. In other words, visual cues to ovulation may exist. However, the authors of that publication also note that the increase in facial attractiveness is clearly subtle and that the mean effect size is small.

SUMMARY OF THE INVENTION

One object of the present invention would be to provide a mechanism that provides an accurate prediction of a fertility window while reducing reliance on more rigorous methods. To better address such concerns, in a first aspect of the invention, an apparatus is presented that predicts the fertility window comprising a period of increased fecundability for a woman based on optical monitoring of facial features, and at the same time, reduces the need for existing methods that require a disciplined and rigorous, repetitive action on the part of the woman.

In an embodiment, the apparatus comprises an image capture device to record plural images comprising facial features of the subject, a memory comprising instructions, and a processor configured to execute the instructions to: receive data corresponding to the recorded images, determine from the data the changes in facial features, and predict a fertility window based on the determination. The fertility window refers to a period of time corresponding to the six (6) days before ovulation, and also the days of ovulation. The use of optical monitoring enables an accurate yet non-invasive, less rigorous approach to predicting the fertility window when compared to other methods of prediction.

In an embodiment, the processor is configured to execute the instructions to determine, from the data, changes in skin tone, changes in symmetry of the facial features, or a combination of both. For instance, skin tone changes in the form of changes in color (e.g., more red coloring to the skin during the fertility window than outside of the fertility window) may indicate that the woman is currently experiencing the fertility window of the menstrual cycle. As another example, changes in the symmetry of the eyes, lips, nose, and/or other facial features may be detected, signifying that the woman is experiencing the fertility window. These are measurements that can be made, accurately, and without the need for body sensors and/or invasive techniques.

In an embodiment, the processor is further configured to execute the instructions to receive supplemental data corresponding to additional fertility prediction methods. Though optional to the performance of the apparatus, the supplemental data may be helpful in improving the probability of accurate and repeatable prediction of the fertility window and/or used to adjust the fertility window to correlate better with these prediction methods. These prediction methods include the use of basal body temperature of the subject, monitoring of luteinizing hormone levels in urine of the subject, analysis of electrolyte in saliva, and cervical mucus monitoring. Using one or more of these methods may serve to improve the accuracy and/or reliability of the optical monitoring features.

In an embodiment, the processor is further configured to execute the instructions to determine when there is a correlation between the supplemental data and the determined changes in the facial features, and based on the determination of when there is a correlation, adjust the period of time of the fertility window or improve the probability of the fertility window where the correlation corresponds to the period of time. In effect, cyclical changes in facial characteristics as determined from the monitoring of facial features over time (e.g., 1-3 months) are mapped with the supplemental data, which may bolster the probability of the prediction and/or result in adjustments to the fertility window. The acquisition of the supplemental data is reduced compared to conventional techniques, enabling less investment in time and/or energy by the woman in family planning matters.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF EMBODIMENTS

Disclosed herein are certain embodiments of a fertility window prediction system that provide optical monitoring of facial features of a woman during her menstrual cycle to predict the fertility window of the woman. As set forth in the background, literature indicates that the perceived attractiveness of a woman's face varies across the menstrual cycle. Optical monitoring is used in certain embodiments of a fertility window prediction system to detect and record changes (e.g., increases) in facial symmetry and changes in skin tone that can be used to develop an accurate and user-friendly ovulation prediction tool for women that can help in the family planning process, including the ability to increase the fecundability of couples with infertility issues. In one embodiment, an apparatus is disclosed that comprises an image capture device to capture (e.g., record) plural images comprising facial features of the subject, a memory comprising instructions, and a processor configured to execute the instructions to receive data corresponding to the recorded images, determine from the data the changes in facial features, and predict a fertility window based on the determination.

Digressing briefly, current offerings of female fertility tests and methods to predict the fertility window are based on detecting luteinizing hormone (LH) in urine, charting the basal body temperature (BBT), looking at electrolyte in saliva, and monitoring the quantity and appearance of the cervical mucus (Cervical Mucus Monitoring or CMM). Almost all tests require disciplined, repetitive action on the part of a woman, and in this way, pose additional stress on a woman who already has to deal with the frustration and disappointment of not getting pregnant while she is actively trying over a longer period of time. In contrast, certain embodiments of a fertility window prediction system overcome or at least mitigate the tedium of previous tests by predicting a woman's fertility window by optically monitoring her facial features during her menstrual cycle.

Having summarized certain features of a fertility window prediction system of the present disclosure, reference will now be made in detail to the description of a fertility window prediction system as illustrated in the drawings. While a fertility window prediction system will be described in connection with these drawings, there is no intent to limit fertility window prediction systems to the embodiment or embodiments disclosed herein. For instance, in the description that follows, the focus is on providing an accurate prediction of the fertility window in increasing the chances of a successful conception for couples with infertility issues (or even to facilitate conception among those not experiencing infertility issues). However, in some embodiments, the fertility prediction window system may be used to reduce the risk of unintended pregnancies for women who depend/rely on natural family planning (or other, reduced reliability contraception methods). Further, although the description identifies or describes specifics of one or more embodiments, such specifics are not necessarily part of every embodiment, nor are all various stated advantages necessarily associated with a single embodiment or all embodiments. On the contrary, the intent is to cover all alternatives, modifications and equivalents included within the spirit and scope of the disclosure as defined by the appended claims. Further, it should be appreciated in the context of the present disclosure that the claims are not necessarily limited to the particular embodiments set out in the description.

Figure 1:
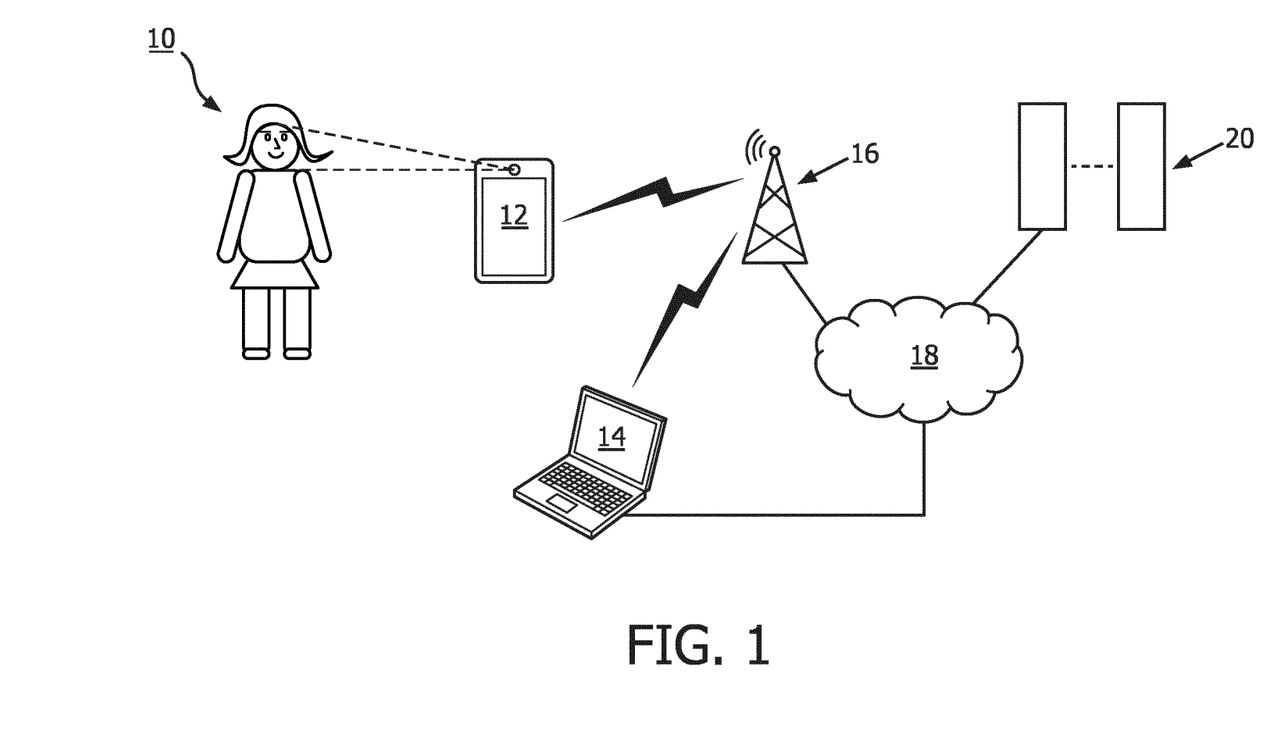
FIG. 1 is a schematic diagram that illustrates an example environment in which a fertility window prediction system is used in accordance with an embodiment of the invention.

Attention is directed to FIG. 1, which illustrates an example environment 10 in which a fertility prediction window system is used in accordance with an embodiment of the invention. It should be appreciated by one having ordinary skill in the art in the context of the present disclosure that the environment 10 is one example among many, and that some embodiments of a fertility prediction window system may be used in environments with fewer, greater, and/or different components that those depicted in FIG. 1. The environment 10 comprises a plurality of devices that enable communication of information throughout one or more networks. The depicted environment 10 comprises electronics devices 12, 14, a cellular network 16, a wide area network 18 (e.g., also described herein as the Internet), and a remote computing system 20. In some embodiments, additional electronic devices may form a part of the environment 10, including a wearable device that is typically worn by the subject (e.g., around the wrist, attached to clothing, etc.), and which comprises a plurality of sensors that track physical activity of the subject (e.g., steps, swim strokes, pedaling strokes, etc.), sense or derive physiological parameters (e.g., heart rate, respiration, skin temperature, etc.) based on the sensor data, and optionally sense various other parameters (e.g., outdoor temperature, humidity, location, etc.) pertaining to the surrounding environment of the wearable device. A representation of such gathered data may be communicated to the subject via an integrated display on the wearable device and/or on another device or devices. Also, such data gathered by the wearable device may be communicated (e.g., continually, periodically, and/or aperiodically) to one or more electronics devices, such as the electronics devices 12 and 14. Such communication may be achieved wirelessly (e.g., using near field communications (NFC) functionality, Blue-tooth functionality, etc.) and/or according to a wired medium (e.g., universal serial bus (USB), etc.). In the depicted example, the electronics device 12 is embodied as a smartphone and the electronics device 14 is embodied as a computer (e.g., laptop, personal computer, tablet, etc.). It should be appreciated that although each electronics device is listed in the singular, some implementations may utilize different quantities for each of the electronics devices 12, 14. Further, in some embodiments, fewer, additional, and/or other types of electronics devices may be used.

The electronic device 12 may be embodied as a smartphone, mobile phone, cellular phone, pager, stand-alone image capture device (e.g., camera), among other handheld computing/communication devices with communication (e.g., wireless communication, including telephony functionality) and built-in, image capture/recording functionality. In the depicted embodiment of FIG. 1, the electronic device 12 is a smartphone. Further discussion of the electronic device 12 is described below in association with FIG. 4.

The electronic device 14 may be embodied as a laptop, personal computer, workstation, personal digital assistant, tablet, notebook device, among other computing devices with communication capability. In some embodiments, the electronic device 14 may be equipped with image capture/recording functionality. In the depicted embodiment of FIG. 1, the electronic device 14 is a laptop with built-in, image capture functionality. Further discussion of the electronic device 14 is described below in association with FIG. 5.

The cellular network 16 may include the necessary infrastructure to enable cellular communications by the electronic device 12 and optionally the electronic device 14. There are a number of different digital cellular technologies suitable for use in the cellular network 16, including: GSM, GPRS, CDMAOne, CDMA2000, Evolution-Data Optimized (EV-DO), EDGE, Universal Mobile Telecommunications System (UMTS), Digital Enhanced Cordless Telecommunications (DECT), Digital AMPS (IS-136/TDMA), and Integrated Digital Enhanced Network (iDEN), among others.

The wide area network 18 may comprise one or a plurality of networks that in whole or in part comprise the Internet. The electronics devices 12, 14 access the devices of the computing system 20 via the Internet 18, which may be further enabled through access to one or more networks including PSTN (Public Switched Telephone Networks), POTS, Integrated Services Digital Network (ISDN), Ethernet, Fiber, DSL/ADSL, among others.

The computing system 20 comprises a plurality of devices coupled to the wide area network 18, including one or more computing devices such as application servers, a computer network, and data storage. As described previously, the computing system 20 may serve as a cloud computing environment (or other server network) for the electronics devices 12, 14, performing processing and data storage on behalf of (or in some embodiments, in addition to) the electronics devices 12, 14. In some embodiments, one or more of the functionality of the computing system 20 may be performed at the respective electronics devices 12, 14 and vice versa.

An embodiment of a fertility window prediction system may comprise one or more devices (or equivalently, one or more apparatuses) of the environment 10. In one embodiment, functionality of the fertility window prediction system may be implemented entirely in the electronic device 12 or the electronic device 14. In one embodiment, functionality of the fertility window prediction system may be implemented in a combination of the electronic devices 12 and 14. In one embodiment, functionality of the fertility window prediction system may be implemented using one or both of the electronic devices 12, 14 and the computing system 20. In some embodiments, devices communicatively integrated as the Internet of Things (IoT) may cooperate to provide image recording, and processing and presentation of the fertility window.

As one example operation, and continuing with reference to FIG. 1, a woman may select a time each day to take a picture of herself. The time chosen each day may be any time, but is preferably a consistent time (e.g., same time each day) and consistent in terms of environmental conditions, such as lighting, magnification, angle, etc. For instance, while preparing for the day in the morning, or seated at a desk at work or home or elsewhere and checking emails and/or social media, the woman may activate an application on the electronic devices 12 or 14. A graphical user interface (GUI) may be presented on the display screen of the electronic devices 12 or 14, which in general, instructs the woman to record the facial image, and more particularly, provides instruction as to proper conditions of the recording. The graphical user interface may show the real-time image of the woman, with prompts presented that instruct the woman as to various image capture conditions, including viewing angle, magnification, and/or lighting. In some embodiments, the image capture conditions may be recommended adjustments to make, or in some embodiments, the adjustments may be made automatically based on sensed conditions and stored for use in subsequent image capture sessions. As consistency in conditions may improve results, the application may prompt the woman with a reminder when a time for image capture is to be taken based on the time the prior day or days the facial image was recorded. In some embodiments, variations in the conditions of the image recording may cause the application to alert the woman and suggest modifications to maintain consistent conditions. In some embodiments, the amount and/or frequency of instructions, alerts, etc. may be set by the woman and, in some embodiments, the instructions may be more rudimentary, or the woman provided an opportunity to activate and deactivate select parameters corresponding to these instructions to the woman. In the depicted example, once ready for image recording, the woman selects the image capture button icon presented in the display screen (e.g., touch-selection) or via other user interface mechanisms, though in some embodiments, a timer may be set to activate image capture process automatically.

Although the above examples illustrate an interactive session between the woman and the GUI aspects of the application running on the electronic devices 12 or 14, in some embodiments, the image capture (recording) process may be more transparent to the woman. That is, the electronic device 12 may be embodied as a standalone image capture device that may be strategically mounted to a location where the facial images may be automatically recorded in consistent manner (time-wise and condition-wise). For instance, the standalone image capture device 12 may be mounted on a vanity mirror, in the shower, above the bathtub, or other locations that the woman would prefer the image capture to regularly take place each morning. The standalone image capture device 12 may communicate (e.g., wirelessly, or via a wired connection) the recorded images to an electronic device 12 embodied as a smartphone or to a laptop 14. The communication may even be achieved manually, such as via manual transfer of a portable storage device (e.g., memory stick, memory card, etc.). Similarly, the woman may configure the application running on a laptop 14 to record images each day for consistent recordings and conditions. The woman may configure (e.g., via a set-up GUI) the laptop image capture functionality to record the facial features upon login by the woman, or upon sensing presence of the woman at a certain time, or time range, each day, where the presence may be indicated by motion/proximity detecting sensors residing within an attached wearable device (or other electronic devices) that communicates to the application the proximity of the woman to the laptop 14. These and/or other mechanisms for recording images may be used as arranged by the woman (or as pre-programmed by the application).

Figure 2:
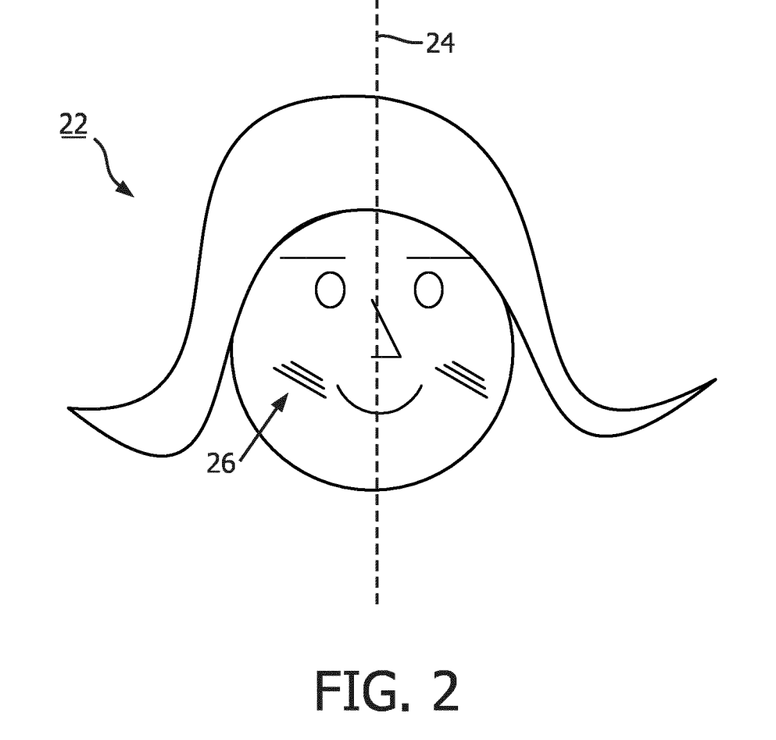
FIG. 2 is a schematic diagram that illustrates logical partitioning of a woman's face by a fertility window prediction system in accordance with an embodiment of the invention.

The recorded images are received by a processing circuit of the electronic devices 12 or 14, and analyzed. For instance, and referring to recorded image 22 in FIG. 2, the woman's face may be logically divided by the application in half, as indicated by the dashed line 24, or partitioned in other ways in some embodiments. In other words, the symmetry of the facial features is analyzed for pre-set features, such as the nose, eyes, mouth and lips. Also, changes in skin tone, as represented by shaded lines 26, are analyzed. For instance, during the fertility window, a reddish or blushed skin tone may occur on the face, including in the cheek regions, though not limited to those locations. Note that the analysis, though schematically represented in FIG. 2, is transparent to the woman. In some embodiments, however, the woman may be provided with feedback of the analysis and afforded an opportunity to dispel some data. For instance, the woman may have incurred a rash on her face, and hence may be provided an opportunity to delete certain conclusions and/or analysis fed back to her via the graphical user interface. The recorded facial images are analyzed on pre-set facial features that focus on any variation and changes in these features and on cyclical changes in skin tone. In one embodiment, the application compares the changes in symmetry between the logical segments of the face. Note that in some embodiments, the analysis may be implemented in another device external to the electronic device 12 or 14. For instance, the electronic devices 12, 14 may access (e.g., via the Internet 18) the computing system 20, where analysis is performed and the prediction results communicated back to the woman via a website hosted by the computing system 20 or communicated back to the electronic device 12 or 14 for presentation on a respective display screen.

Figure 3A:
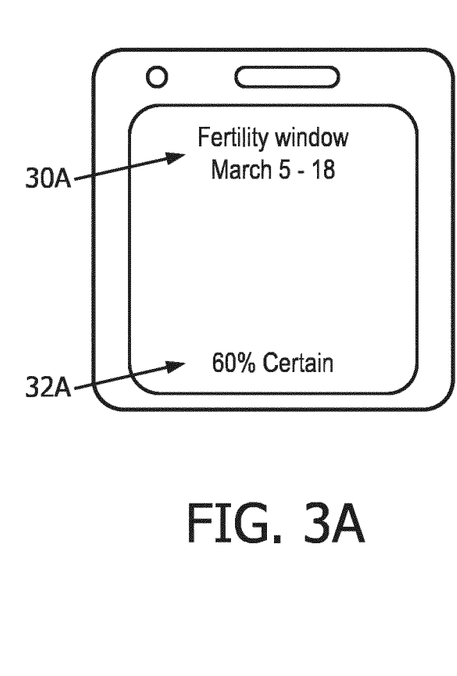
FIGS. 3A-3C are screen diagrams that illustrate a visual representation of the fertility prediction window and percent probability as presented by a fertility window prediction system in accordance with an embodiment of the invention.
Figure 3B:
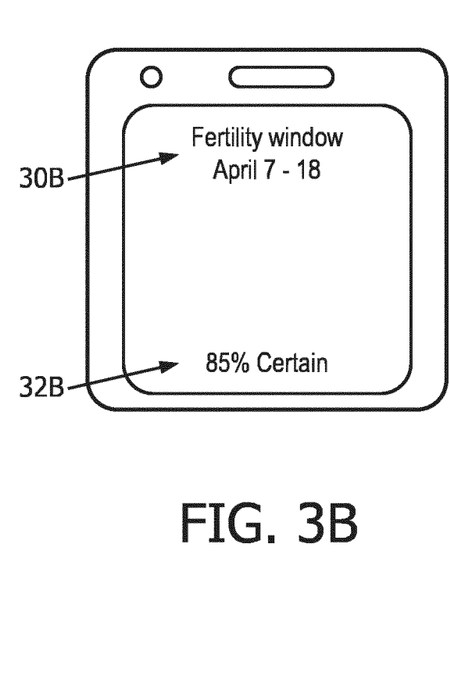
Figure 3C:
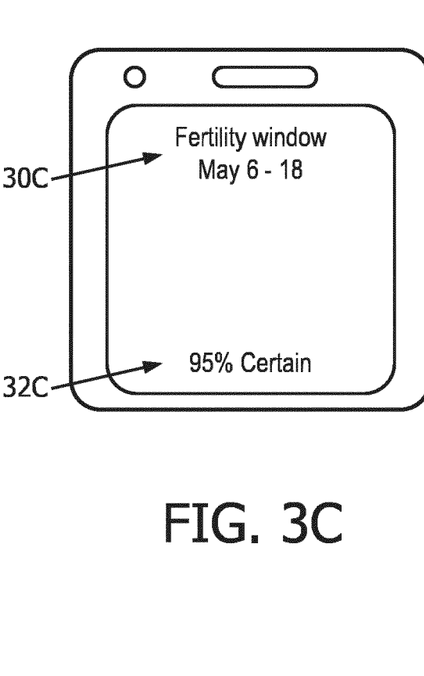

Note that the results may be shielded from the woman until a sufficient time period has elapsed where there is a high degree of confidence (sufficient confidence in the probability of the fertility prediction window). Alternatively, in some embodiments, the visualization of the fertility window may be progressively altered as more images are received and analyzed. For instance, and referring to FIGS. 3A-3C, a graphical user interface may be presented (e.g., on a display screen of the electronic devices 12 and/or 14), with the fertility window presented as a range of dates 30 (e.g., 30A, 30B, 30C) by alphanumeric values (as depicted in FIGS. 3A-3B), or in some embodiments, as highlighted dates in a displayed calendar (e.g., grid of days per month). In some embodiments, a value 32 (e.g., 32A, 32B, 32C) may be presented in conjunction with the prediction window 30 signifying the confidence in the prediction (e.g., 60% certain in FIG. 3A, 85% certain in FIG. 3B, and 95% certain in FIG. 3C). In some embodiments, a textual or graphical warning may be presented with the results that explain the reliability and/or accuracy of the results (e.g., "prediction window currently based on analysis of "X" months data). In some embodiments, changes in applied gray scale to the visualization of the fertility window may be presented to both reveal a prediction window and reveal the confidence of the prediction. For instance, the fertility window based on the first month of analysis may appear as a somewhat grayed-out font and/or grayed-out gridlines, whereas the fertility window based on the second month presented with cleaner and darker font and/or gridlines, and the results from a third month of analysis may appear as solid, dark font or gridlines, representing to the woman a higher degree of confidence in the results. The period of time leading up to sufficient confidence in the prediction window is referred to hereinafter as a training period, where the optical monitoring is trained to provide increasingly accurate fertility window predictions as data is accumulated. Note that although three (3) screens are presented in FIGS. 3A-3C corresponding to the presented certainty in the fertility window prediction, this is merely for example, and the prediction window accuracy may be greater or less over the same or different time period of the training period in some embodiments.

During the training period, supplemental data may be received by the electronic device 12 or 14 in some embodiments. Supplemental data comprises data from other fertility tests to predict the fertility window, including basal body temperature (BBT) charting, cervical mucus monitoring (CMM), monitoring of luteinizing hormone (LH) levels in urine, and analysis of electrolyte in saliva. One or more of the data may be manually entered at the user interface of the electronic devices 12 or 14, and/or electronically downloaded via access to such data from a remote system (e.g., from the computing system 20) and/or locally from a local fertility prediction application running on one of the electronic devices 12 or 14. For instance, the woman may use online fertility testing methods, where the data from those online systems may be accessed by the application. The results of the data analysis of the recorded facial image features are mapped to the supplemental data. Cyclic changes in the analyzed facial features (e.g., the symmetry and skin tone changes) are mapped with the supplemental data. In other words, the fertility window prediction application determines whether there is a correlation between the supplemental data and the determined changes in facial features, and based on the determination of when there is a correlation, adjust the period of time of the prior-predicted fertility window (e.g., based on the application alone) or improve a probability of the fertility window where the correlation corresponds to the period of time already determined by the application (e.g., where the mapping reveals that the time period predicted to be the fertility window based on optical monitoring matches the time period the time period predicted by other methods). That is, based on the determination of when there is a correlation, the period of time of the predicted fertility window is adjusted to match a period time predicted by the additional fertility prediction methods or the other fertility tests. Even in the former case, the probability that the fertility window is as predicted is improved since there is optical monitoring data and the supplemental data to substantiate the period of time of the predicted fertility window.

Having described an example of operations of an embodiment of a fertility window prediction system, attention is directed to FIG. 4, which illustrates an example electronic device 12 embodied as a smartphone (hereinafter, referred to as smartphone 12). It should be appreciated by one having ordinary skill in the art that the logical block diagram depicted in FIG. 4 and described below is one example, and that other designs may be used in some embodiments that incorporate fertility window prediction software. The smartphone 12 comprises at least two different processors, including a baseband processor (BBP) 34 and an application processor (APP) 36. As is known, the baseband processor 34 primarily handles baseband communication related tasks and the application processor 36 generally handles inputs and outputs and all applications other than those directly related to baseband processing. The baseband processor 34 comprises a dedicated processor for deploying functionality associated with a protocol stack (PROT STK) 38, such as a GSM (Global System for Mobile communications) protocol stack, among other functions. The application processor 36 comprises a multi-core processor for running applications (APPS) 40, among other functions. The baseband processor 34 and application processor 36 have respective associated memory (e.g., MEM) 42, 44, including random access memory (RAM), Flash memory, etc., and peripherals, and a running clock.

More particularly, the baseband processor 34 may deploy functionality of the protocol stack 38 to enable the smartphone 12 to access one or a plurality of wireless network technologies, including WCDMA (Wideband Code Division Multiple Access), CDMA (Code Division Multiple Access), EDGE (Enhanced Data Rates for GSM Evolution), GPRS (General Packet Radio Service), Zigbee (e.g., based on IEEE 802.15.4), Bluetooth, Wi-Fi (Wireless Fidelity, such as based on IEEE 802.11), and/or LTE (Long Term Evolution), among variations thereof and/or other telecommunication protocols, standards, and/or specifications. The baseband processor 34 manages radio communications and control functions, including signal modulation, radio frequency shifting, and encoding. The baseband processor 34 comprises, or may be coupled to, a radio (e.g., RF front end) 46 and/or a GSM modem having one or more antennas, and analog and digital baseband circuitry (ABB, DBB, respectively in FIG. 4). The radio 46 comprises a transceiver and a power amplifier to enable the receiving and transmitting of signals of a plurality of different frequencies, enabling access to the cellular network 16. The analog baseband circuitry is coupled to the radio 46 and provides an interface between the analog and digital domains of the GSM modem. The analog baseband circuitry comprises circuitry including an analog-to-digital converter (ADC) and digital-to-analog converter (DAC), as well as control and power management/distribution components and an audio codec to process analog and/or digital signals received (indirectly via the application processor 36 or directly) from the smartphone user interface 48 (e.g., microphone, earpiece, ring tone, vibrator circuits, etc.). The ADC digitizes any analog signals for processing by the digital baseband circuitry. The digital baseband circuitry deploys the functionality of one or more levels of the GSM protocol stack (e.g., Layer 1, Layer 2, etc.), and comprises a microcontroller (e.g., microcontroller unit or MCU) and a digital signal processor (DSP) that communicate over a shared memory interface (the memory comprising data and control information and parameters that instruct the actions to be taken on the data processed by the application processor 36). The MCU may be embodied as a RISC (reduced instruction set computer) machine that runs a real-time operating system (RTIOS), with cores having a plurality of peripherals (e.g., circuitry packaged as integrated circuits) such as RTC (real-time clock), SPI (serial peripheral interface), I2C (inter-integrated circuit), UARTs (Universal Asynchronous Receiver/Transmitter), devices based on IrDA (Infrared Data Association), SD/MMC (Secure Digital/Multimedia Cards) card controller, keypad scan controller, and USB devices, GPRS crypto module, TDMA (Time Division Multiple Access), smart card reader interface (e.g., for the one or more SIM (Subscriber Identity Module) cards), timers, and among others. For receive-side functionality, the MCU instructs the DSP to receive, for instance, in-phase/quadrature (I/Q) samples from the analog baseband circuitry and perform detection, demodulation, and decoding with reporting back to the MCU. For transmit-side functionality, the MCU presents transmittable data and auxiliary information to the DSP, which encodes the data and provides to the analog baseband circuitry (e.g., converted to analog signals by the DAC).

The application processor 36 operates under control of an operating system (OS) 50 that enables the implementation of a plurality of user applications 40. The application processor 36 may be embodied as a System on a Chip (SOC), and supports a plurality of multimedia related features including web browsing to access one or more computing devices of the computing system 20 that are coupled to the Internet, email, multimedia entertainment, games, etc. For instance, the application processor may execute interface software (e.g., middleware, such as a browser with or operable in association with one or more application program interfaces (APIs)) to enable access to a cloud computing framework or other networks to provide remote data access/storage/processing, and through cooperation with an embedded operating system, access to calendars, location services, reminders, etc. For instance, in some embodiments, the fertility window prediction system may operate using cloud computing, where the processing and storage of user data (e.g., from supplemental data accessible from the computing system 20, including data from BBT tests, LH tests, electrolyte tests, CCM tests performed and recorded at a health facility, or performed and recorded at home and uploaded from a computing device and stored in storage devices of the computing system 20) and/or the determination of facial feature changes and prediction of a fertility window based on the changes (e.g., based on image data provided over the network(s) 16, 18 may be achieved by one or more devices of the computing system 20. The application processor 36 generally comprises a processor core (Advanced RISC Machine or ARM), and further comprises or may be coupled to multimedia modules (for decoding/encoding pictures, video, and/or audio), a graphics processing unit (GPU), communication interfaces (COMM) 52, and device interfaces. The communication interfaces 52 may include wireless interfaces, including a Bluetooth (BT) (and/or Zigbee in some embodiments) module that enables wireless communication with an electronic device, including a wearable device, the electronic device 14, among others, and a Wi-Fi module for interfacing with a local 802.11 network. The application processor 36 further comprises, or is coupled to, a global navigation satellite systems (GNSS) transceiver or receiver (GNSS) 54 for access to a satellite network to provide location services. The device interfaces coupled to the application processor 36 may include the user interface 48, including a display screen. The display screen may be embodied in one of several available technologies, including LCD or Liquid Crystal Display (or variants thereof, such as Thin Film Transistor (TFT) LCD, In Plane Switching (IPS) LCD)), light-emitting diode (LED)-based technology, such as organic LED (OLED), Active-Matrix OLED (AMO-LED), or retina or haptic-based technology. For instance, the display screen may be used to present web pages and/or other documents received from the computing system 20 and/or the display screen may be used to present information in graphical user interfaces (GUIs) rendered locally in association with the applications 40. Other user interfaces 48 include a keypad, microphone, speaker, ear piece connector, I/O interfaces (e.g., USB (Universal Serial Bus)), SD/MMC card, among other peripherals. Also coupled to the application processor is an image capture device (IMAGE CAPTURE) 56. The image capture device 56 comprises an optical sensor (e.g., a charged coupled device (CCD) or a complementary metal-oxide semiconductor (CMOS) optical sensor). The image capture device 56 may be used to detect and record changes in facial symmetry and/or skin tone. Also included is a power management device 58 that controls and manages operations of a battery 60. The components described above and/or depicted in FIG. 4 share data over one or more busses, and in the depicted example, via data bus 62. It should be appreciated by one having ordinary skill in the art, in the context of the present disclosure, that variations to the above may be deployed in some embodiments to achieve similar functionality.

In the depicted embodiment, the application processor 36 runs plural applications 40, including fertility window prediction software comprising facial feature detection software (FACE FTR DTCT) 64, analysis software (ANALYSIS) 66, fertility window prediction software (FW PREDICT) 68, mapping software (MAPPING) 70, and GUI software (GUI) 72, the latter providing for the feedback of the fertility window and/or image capture set-up, as described previously. Note that GUI software 72 may be used to render content on the UI 48 (e.g., display screen) from other applications as well in some embodiments. The facial feature detection software 64 operates in conjunction with the image capture device 56 to perform remote photoplethysmography (PPG) to detect skin tone changes and also implement facial recognition technology to detect changes in symmetry of pre-set facial features, including the eyes, nose, and mouth. Such PPG technology for skin tone changes may incorporate commercially available Philips Vital Signs Camera algorithms that amplify skin color changes (e.g., by analyzing frequency of color changes) that result from blood flow changes in the blood vessels beneath the skin surfaces. These changes may be undetectable to the human eye, including invisible microblushes. Likewise, symmetry of the pre-set facial features may be detected using commercially available facial recognition software. The analysis software 66, which in some embodiments may be a component of the facial feature detection software 64, logically partition the face to determine symmetry, and is further configured to associate the detected changes to calendar days, using for instance calendar software incorporated in the analysis software 66 or accessed from an events calendar application stored in memory 44. In other words, the analysis software 66 compares and records the changes in skin tone and symmetry, and associates those changes with calendar days from month to month. The fertility window prediction software 68 looks to the associations of the cyclical changes and computes a probability of the fertility window based on the monitored changes. For instance, based on determining that the image data reveals consistently redder facial blushes and increased symmetry during a period of time each month, the fertility window prediction software assesses the probability of those changes occurring the existing and following months, and cooperates with the GUI software 72 to present the fertility window to the woman. The mapping software 70 is optional, and may be used to amend or corroborate (e.g., increase or decrease the probability of the veracity of the fertility window) the fertility window based on supplemental data stored in memory 44 (or accessed from other devices) pertaining to BBT charting, CMM, LH levels, and/or electrolytes in the saliva. For instance, during the training period, say 1-3 months, the fertility window prediction software may predict the fertility window based on the supplemental data, after which the optical monitoring may continue predictions without the need for the other fertility window prediction methods (or in some embodiments, with reduced need). By providing the fertility window prediction, the woman can assess the best moments for sexual intercourse (or when to refrain from sex for family planning purposes). Note that functionality of the software modules 64, 66, 68, 70, and 72 of the applications 40 may be combined in some embodiments, or further distributed among additional modules. In some embodiments, the execution of the software modules 64, 66, 68, and 70 may be distributed among plural devices.

Figure 4:
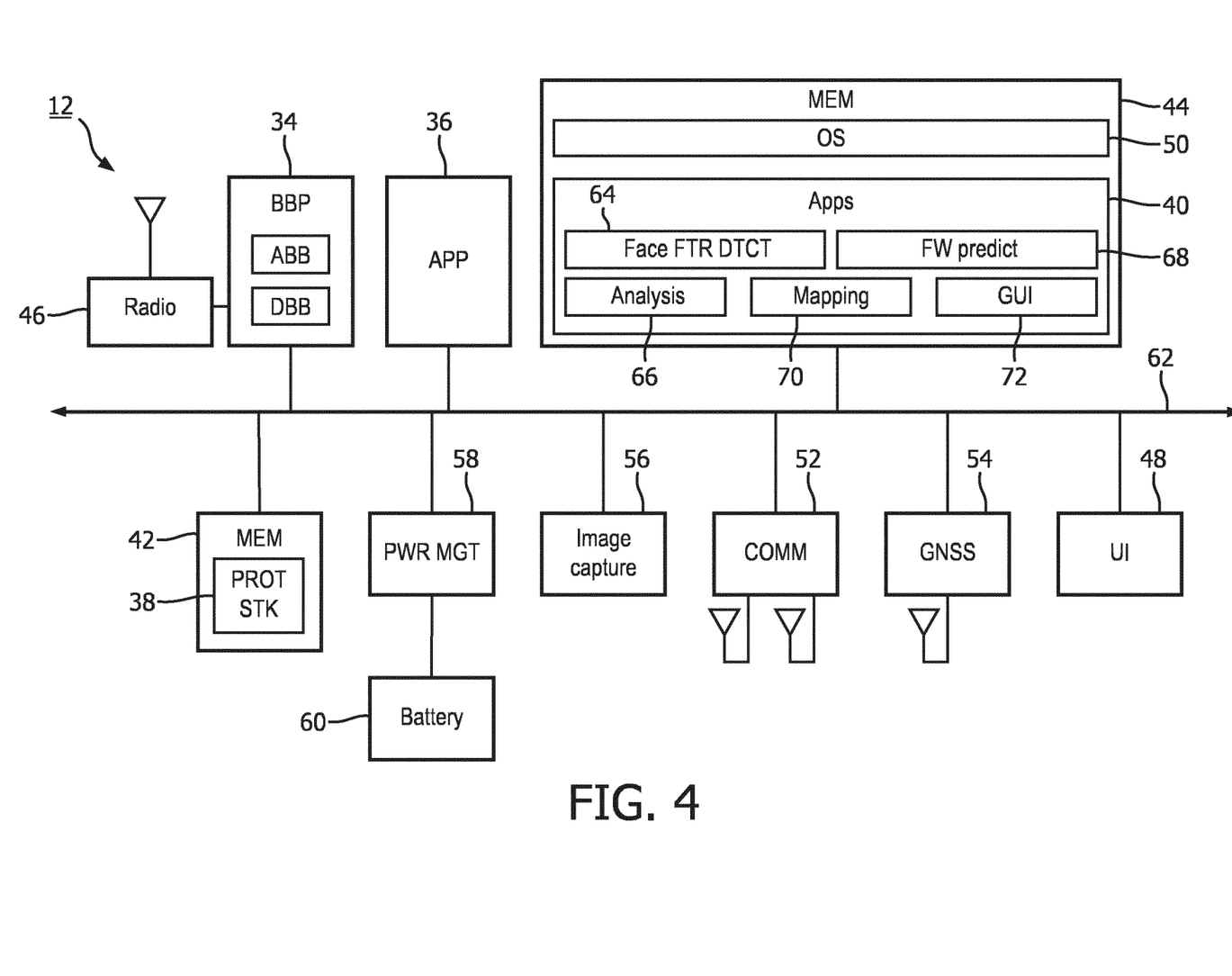
FIG. 4 is a block diagram that illustrates an embodiment of an electronic device in the environment of FIG. 1 for implementing a fertility window prediction method in accordance with an embodiment of the invention.
Figure 5:
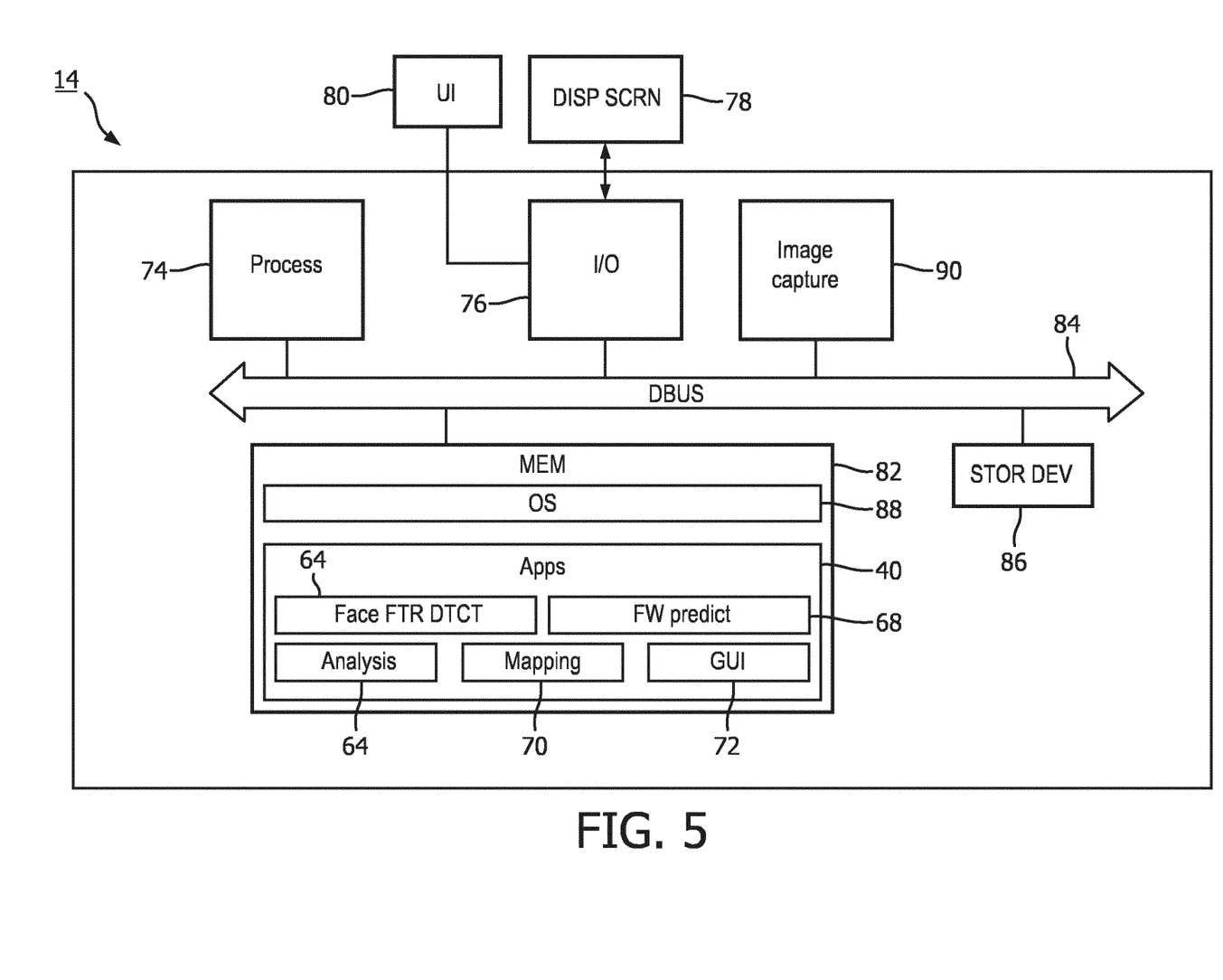
FIG. 5 is a block diagram that illustrates an embodiment of another electronic device in the environment of FIG. 1 for implementing a fertility window prediction method in accordance with an embodiment of the invention.

Although the description for FIG. 4 is in the context of the smartphone 12 used for handling fertility window prediction, as set forth above, other and/or additional devices, including electronic device 14, may be used to perform these functions. Referring to FIG. 5, shown is a logical block diagram of an electronic device embodied as a laptop (the electronic device 14 referred to hereinafter as the laptop 14). One having ordinary skill in the art should appreciate in the context of the present disclosure that the example laptop 14 is merely illustrative of one embodiment, and that some embodiments of electronic devices 14 may comprise fewer or additional components, and/or some of the functionality associated with the various components depicted in FIG. 5 may be combined, or further distributed among additional modules or computing devices, in some embodiments. Note that in some embodiments, computing devices of the computing system 20 may comprise a similar architecture. The laptop 14 comprises a computer architecture, and it should be appreciated that certain well-known components of computers are omitted here to avoid obfuscating relevant features of the laptop 14. In one embodiment, the laptop 14 comprises one or more processors, such as processor 74 (PROCES), input/output (I/O) interface(s) 76 (I/O), a display screen 78 (DISP SCRN) and other user interfaces 80 (e.g., keyboard, mouse, microphone, headset, and memory 82 (MEM), all coupled to one or more data busses, such as data bus 84 (DBUS). In some embodiments, the display screen 78 (and/or user interface (UI)) 80 may be coupled directly to the data bus 84. The memory 82 may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory 82 may store a native operating system, one or more native applications, emulation systems, or emulated applications for any of a variety of operating systems and/or emulated hardware platforms, emulated operating systems, etc. In some embodiments, a separate storage device (STOR DEV) 86 may be coupled to the data bus 84 or as a network-connected device (or devices) via the I/O interfaces 76 and the Internet 18. The storage device 86 may be embodied as persistent memory (e.g., optical, magnetic, and/or semiconductor memory and associated drives) to store user data (e.g., data from other fertility window prediction methods entered manually or otherwise received via the I/O interfaces 76). The laptop 14 also comprise an image capture device 90, which is similar to image capture device 56 described in association with FIG. 4 and omitted here for brevity.

In the embodiment depicted in FIG. 5, the memory 82 comprises an operating system 88 (OS), and applications (APPS) 40 that include the fertility window prediction software comprising facial feature detection software (FACE FTR DTCT) 64, analysis software (ANALYSIS) 66, fertility window prediction software (FW PREDICT) 68, mapping software (MAPPING) 70, and GUI software (GUI) 72. The fertility window prediction software is described above in conjunction with FIG. 4, and is omitted here for brevity.

Execution of the applications 40 (and associated software modules 64, 66, 68, 70, and 72) may be implemented by the processor 74 under the management and/or control of the operating system 88. The processor 74 may be embodied as a custom-made or commercially available processor, a central processing unit (CPU) or an auxiliary processor among several processors, a semiconductor based microprocessor (in the form of a microchip), a macroprocessor, one or more application specific integrated circuits (ASICs), a plurality of suitably configured digital logic gates, and/or other well-known electrical configurations comprising discrete elements both individually and in various combinations to coordinate the overall operation of the laptop 14.

The I/O interfaces 76 comprise hardware and/or software to provide one or more interfaces to the user interfaces (e.g., UI 80, display screen 78), the Internet 18 (e.g., to the devices of the computing system 20), as well as to other devices such as the electronic device 12 and/or wearable devices. In other words, the I/O interfaces 76 may comprise any number of interfaces for the input and output of signals (e.g., analog or digital data) for conveyance of information (e.g., data) over various networks and according to various protocols and/or standards. In one embodiment, the I/O interfaces 76 may comprise, or be similar to, the wireless communication hardware and/or software used in the smartphone 12.

When certain embodiments of the laptop 14 are implemented at least in part with software (including firmware), as depicted in FIG. 5, it should be noted that the software (e.g., such as the applications 40 and associated software modules 64, 66, 68, 70, and 72) can be stored on a variety of non-transitory computer-readable medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the laptop 14 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), relays, contactors, etc.

Figure 6:
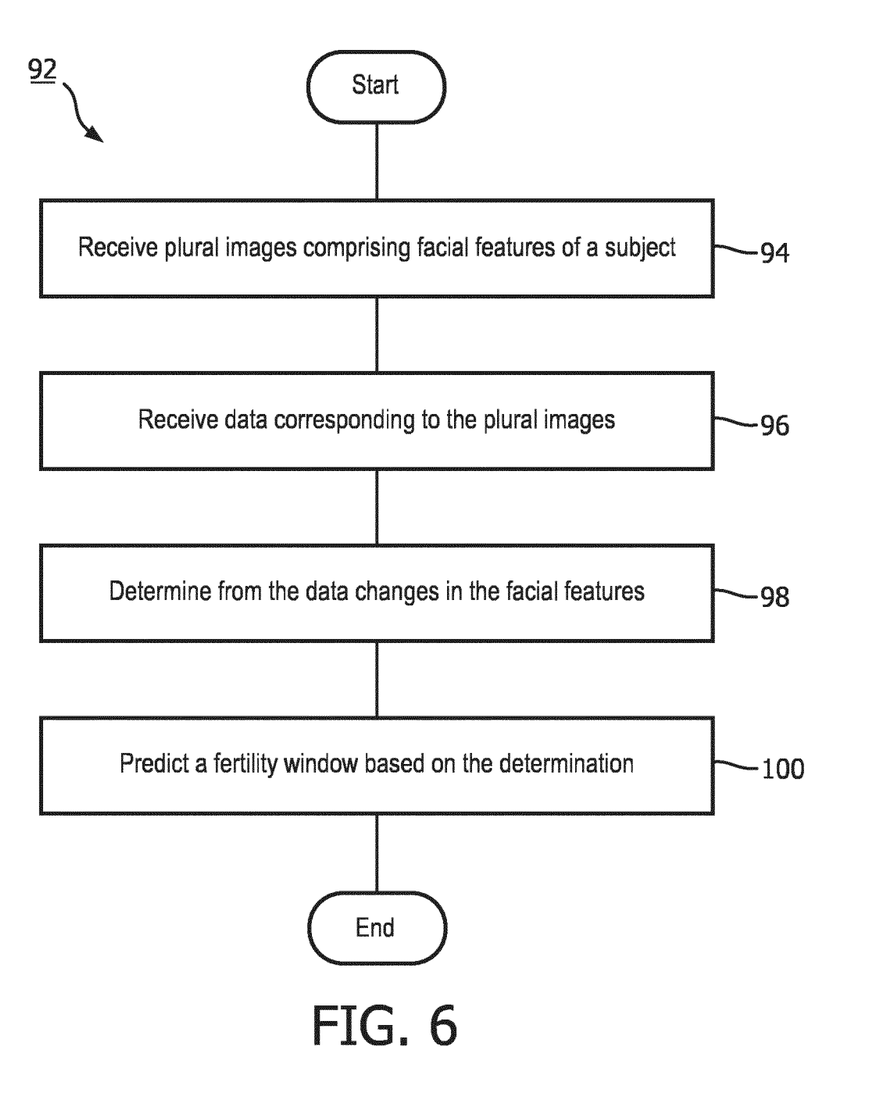
FIG. 6 is a flow diagram that illustrates a fertility window prediction method in accordance with an embodiment of the invention.

In view of the description above, it should be appreciated that one embodiment of a fertility window prediction method, depicted in FIG. 6 and referred to as a method 92 and encompassed between start and end designations, comprises receiving plural images comprising facial features of a subject (94); receiving data corresponding to the plural images (96); determining from the data changes in the facial features (98); and predicting a fertility window based on the determination, the fertility window comprising a period of time of increased fecundability for the subject (100).

Any process descriptions or blocks in the flow diagram of FIG. 6 should be understood as representing modules, segments, or portions of code which include one or more executable instructions for implementing specific logical functions or steps in the process, and alternate implementations are included within the scope of an embodiment of the present invention in which functions may be executed substantially concurrently, and/or additional logical functions or steps may be added, depending on the functionality involved, as would be understood by those reasonably skilled in the art of the present invention.

In one embodiment, a claim to an apparatus is disclosed, comprising: an image capture device configured to record plural images comprising facial features of a subject; memory comprising instructions; and a processor configured to execute the instructions to: receive data corresponding to the recorded plural images; determine from the data changes in the facial features; and predict a fertility window based on the determination, the fertility window comprising a period of time of increased fecundability for the subject.

An apparatus according to the prior claim, wherein the processor is configured to execute the instructions to determine from the data changes in skin tone.

An apparatus according to any one of the preceding claims, wherein the processor is configured to execute the instructions to determine from the data changes in symmetry of the facial features.

An apparatus according to any one of the preceding claims, wherein the processor is configured to execute the instructions to determine from the data changes in skin tone and changes in symmetry of the facial features.

An apparatus according to any one of the preceding claims, wherein the processor is further configured to execute the instructions to receive supplemental data corresponding to additional fertility prediction methods.

An apparatus according to the prior claim, wherein the processor is further configured to execute the instructions to receive the supplemental data comprising one or any combination of basal body temperature of the subject, luteinizing hormone levels in urine of the subject, and cervical mucus data of the subject. In a further embodiment, the processor is further configured to execute the instructions to determine when there is a correlation between the supplemental data and the determined changes in the facial features, and based on the determination of when there is a correlation, adjust the period of time of the fertility window or improve a probability of the fertility window where the correlation corresponds to the period of time.

An apparatus according to the prior claim, wherein the processor is configured to execute the instructions to predict the fertility window based on the determination and the correlation.

An apparatus according to any one of the preceding claims, wherein the processor is configured to execute the instructions to determine from the data the changes in the facial features according to analysis of a predetermined set of facial features.

In one embodiment, a claim to a method is disclosed, comprising: receiving plural images comprising facial features of a subject; receiving data corresponding to the plural images; determining from the data changes in the facial features; and predicting a fertility window based on the determination, the fertility window comprising a period of time of increased fecundability for the subject.

A method according to the prior claim, wherein determining from the data changes in the facial features comprises determining from the data one or a combination of changes in skin tone and changes in symmetry of the facial features.

A method according to any one of the preceding claims, further comprising receiving supplemental data corresponding to additional fertility prediction methods.

A method according to the prior claim, wherein receiving the supplemental data comprises receiving one or any combination of basal body temperature of the subject, luteinizing hormone levels in urine of the subject, and cervical mucus data of the subject.

A method according to the prior claim, further comprising determining when there is a correlation between the supplemental data and the determined changes in the facial features, and based on the determination of when there is a correlation, adjusting the period of time of the fertility window or improving a probability of the fertility window where the correlation corresponds to the period of time, wherein the fertility window is predicted based on the determination and the correlation.

In one embodiment, a claim to a non-transitory computer readable medium encoded with instructions executable by a processor that causes the processor to: receive plural images comprising facial features of a subject; receive data corresponding to the plural images; determine from the data changes in the facial features; and predict a fertility window based on the determination, the fertility window comprising a period of time of increased fecundability for the subject.

While the invention has been illustrated and described in detail in the drawings and foregoing description, such illustration and description are to be considered illustrative or exemplary and not restrictive; the invention is not limited to the disclosed embodiments. For example, as described previously, the image capture and processing and/or display of the fertility window may be performed in a single electronic device (e.g., smartphone, laptop, tablet, etc.), or via plural devices (stand-alone camera, smartphone, laptop, tablet, remote computing device, etc.). In some embodiments, a wearable device with image capture functionality and a display screen may implement the functionality of the fertility window prediction system. Though described using visual feedback to the woman, in some embodiments, audible feedback and/or tactile feedback, such as through a wearable device or other electronic device or attached peripheral (e.g., headset, ear phones, etc.), may communicate the fertility window to the woman. Other variations to the disclosed embodiments can be understood and effected by those skilled in the art in practicing the claimed invention, from a study of the drawings, the disclosure, and the appended claims. Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

The invention claimed is:

1. An apparatus, comprising:
an image capture device configured to record plural images comprising facial features of a subject;
a display;
a memory comprising instructions; and
a processor configured to execute the instructions to performs acts of:
receiving data over a number of months, the data corresponding to the recorded plural images;
analyzing by the processor the data corresponding to the recorded plural images;
determining, by the processor from the data analyzing act, cyclical changes in the facial features and associate the cyclical changes with calendar days from month to month to determine dates of a fertility window, the cyclical changes including changes undetectable to a human eye;
based on the determining act, predicting by the processor the fertility window and form a prediction signal including the dates of the fertility window and a confidence level indicating reliability of the prediction signal;
repeating the receiving, determining and predicting acts during a training period until a predetermined time period has elapsed where the confidence level increases from month to month until the confidence level reaches a predetermined sufficient confidence level, the fertility window being a period of time of increased fecundability for the subject relative to a different period of time;
shielding the prediction signal during the training period to prevent display of the prediction signal on the display and allow increase of the confidence level to increased confidence levels greater than the predetermined sufficient confidence level;
outputting the prediction signal to the display for visualization of the fertility window on the display including the dates of the fertility window and the increased confidence levels associated with the dates of the fertility window;
displaying on the display the visualization of the fertility window including the dates of the fertility window, the increased confidence levels associated with the dates of the fertility window, and the number of months; and progressively altering the visualization of the fertility window as more images are received and analyzed including altering the dates of the fertility window to display new dates of the fertility window and altering the confidence level to display the increased confidence levels, wherein the cyclical changes in the facial features include changes in symmetry of the facial features.

2. The apparatus of claim 1, wherein the processor is configured to execute the instructions to determine from the data changes in skin tone.

3. The apparatus of claim 1, wherein the processor is further configured to execute the instructions to receive supplemental data corresponding to additional fertility prediction methods.

4. The apparatus of claim 3, wherein the processor is further configured to execute the instructions to receive the supplemental data comprising at least one of basal body temperature of the subject, luteinizing hormone levels in urine of the subject, data corresponding to electrolyte in saliva, and cervical mucus data of the subject.

5. The apparatus of claim 3, wherein the processor is further configured to execute the instructions to determine when there is a correlation between the supplemental data and the determined cyclical changes in the facial features, and based on the determination of when there is a correlation, adjust the period of time of the predicted fertility window to match a period time predicted by the additional fertility prediction methods.

6. The apparatus of claim 5, wherein the processor is configured to execute the instructions to predict the fertility window based on the determination and the correlation.

7. The apparatus of claim 1, wherein the processor is configured to execute the instructions to determine from the data the cyclical changes in the facial features according to analysis of a predetermined set of facial features.

8. The apparatus of claim 1, wherein the increased confidence level is at least one of an alphanumeric indication and a change in appearance of the prediction signal displayed on the display.

9. A method, comprising acts of:
receiving by an image capture device plural images comprising facial features of a subject;
receiving by a processor data over a number of months, the data corresponding to the plural images;
analyzing by the processor the data corresponding to the recorded plural images;
determining, by the processor from the data analyzing act, cyclical changes in the facial features;
associating by the processor the cyclical changes with calendar days from month to month to determine dates of the fertility window, the cyclical changes including changes undetectable to a human eye;
predicting by the processor a fertility window based on the determination and forming a prediction signal including the dates of the fertility window and a confidence level indicating reliability of the prediction signal;
repeating the receiving, determining, associating and predicting acts during a training period until a predetermined time period has elapsed where the confidence level increases from month to month until the confidence level reaches a predetermined sufficient confidence level, the fertility window being a period of time of increased fecundability for the subject relative to a different period of time;
shielding by the processor the prediction signal during the training period to prevent display of the prediction signal on a display and allow increase of the confidence level to increased confidence levels greater than the predetermined sufficient confidence level;
outputting by the processor the prediction signal to the display for visualization of the fertility window on the display including the dates of the fertility window and the increased confidence levels associated with the dates of the fertility window;
displaying on the display the visualization of the fertility window including the dates of the fertility window, the increased confidence levels associated with the dates of the fertility window, and the number of months; and
progressively altering the visualization of the fertility window as more images are received and analyzed including altering the dates of the fertility window to display new dates of the fertility window and altering the confidence level to display the increased confidence levels,
wherein the cyclical changes in the facial features include changes in symmetry of the facial features.

10. The method of claim 9, wherein the determining act comprises determining from the data of changes in skin tone of the facial features.

11. The method of claim 9, further comprising receiving supplemental data corresponding to additional fertility prediction methods.

12. The method of claim 11, wherein receiving the supplemental data comprises receiving at least one of basal body temperature of the subject, luteinizing hormone levels in urine of the subject, and cervical mucus data of the subject.

13. The method of claim 12, further comprising determining when there is a correlation between the supplemental data and the determined cyclical changes in the facial features, and based on the determination of when there is a correlation, adjusting the period of time of the fertility window to match a period time predicted by the additional fertility prediction methods.

14. A non-transitory computer readable medium encoded with instructions executable by a processor that causes the processor to performs acts of:
receiving plural images comprising facial features of a subject;
receiving data over a number of months, the data corresponding to the plural images;
analyzing by the processor the data corresponding to the recorded plural images;
determining, by the processor from the data analyzing act, cyclical changes in the facial features;
associating the cyclical changes with calendar days from month to month to determine dates of the fertility window, the cyclical changes including changes undetectable to a human eye;
predicting a fertility window based on the determination and form a prediction signal including the dates of the fertility window and a confidence level indicating reliability of the prediction signal;
repeating the receiving, determining, associating and predicting acts during a training period until a predetermined time period has elapsed where the confidence level increases from month to month until the confidence level, the fertility window being a period of time of increased fecundability for the subject relative to a different period of time;

shielding the prediction signal during the training period to prevent display of the prediction signal on a display and allow increase of the confidence level to increased confidence levels greater than the predetermined sufficient confidence level;

outputting the prediction signal to the display for visualization of the fertility window on the display including the dates of the fertility window and the increased confidence levels associated with the dates of the fertility window; and causing the display to display the visualization of the fertility window including the dates of the fertility window, the increased confidence levels associated with the dates of the fertility window, and the number of months; and progressively altering the visualization of the fertility window as more images are received and analyzed including altering the dates of the fertility window to display new dates of the fertility window and altering the confidence level to display the increased confidence levels, wherein the cyclical changes in the facial features include changes in symmetry of the facial features.

15. The non-transitory computer readable medium of claim 14, wherein the determine from the data cyclical changes in the facial features comprises determine from the data of changes in skin tone of the facial features.

16. The non-transitory computer readable medium of claim 14, further comprising instructions executable by the processor that cause the processor to receive supplemental data corresponding to additional fertility prediction methods.

17. The non-transitory computer readable medium of claim 16, wherein receive the supplemental data further includes receive at least one combination of basal body temperature of the subject, luteinizing hormone levels in urine of the subject, and cervical mucus data of the subject.

18. The non-transitory computer readable medium of claim 17, further comprising instructions executable by the processor that cause the processor to determine when there is a correlation between the supplemental data and the determined cyclical changes in the facial features, and based on the determination of when there is a correlation, adjust the period of time of the fertility window to match a period time predicted by the additional fertility prediction methods.

* * * * *